(12) United States Patent
Wong et al.

(10) Patent No.: US 11,432,831 B2
(45) Date of Patent: Sep. 6, 2022

(54) TARGETING GUIDE AND METHOD FOR AN IMPLANT

(71) Applicant: Wright Medical Technology, Inc., Memphis, TN (US)

(72) Inventors: Kian-Ming Wong, Lakeland, TN (US); George Awtrey, Barlett, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 488 days.

(21) Appl. No.: 16/322,246

(22) PCT Filed: Sep. 30, 2016

(86) PCT No.: PCT/US2016/054788
§ 371 (c)(1),
(2) Date: Jan. 31, 2019

(87) PCT Pub. No.: WO2018/063329
PCT Pub. Date: Apr. 5, 2018

(65) Prior Publication Data
US 2021/0275195 A1    Sep. 9, 2021

(51) Int. Cl.
    *A61B 17/17*   (2006.01)
    *A61B 17/72*   (2006.01)
    *A61B 17/80*   (2006.01)

(52) U.S. Cl.
CPC .......... *A61B 17/17* (2013.01); *A61B 17/1725* (2013.01); *A61B 17/1728* (2013.01); *A61B 17/7291* (2013.01); *A61B 17/8057* (2013.01)

(58) Field of Classification Search
CPC . A61B 17/17; A61B 17/1725; A61B 17/1728; A61B 17/8894
See application file for complete search history.

(56) References Cited

U.S. PATENT DOCUMENTS

| 2,614,559 A | 10/1952 | Livingston |
| 4,911,153 A | 3/1990 | Border |
| (Continued) | | |

FOREIGN PATENT DOCUMENTS

| CA | 2646726 A1 | 9/2007 |
| EP | 1759643 A1 | 3/2007 |
| WO | WO2003059181 A1 | 6/2003 |

OTHER PUBLICATIONS

International Search Report and Written Opinion issued in connection with International Patent Application No. PCT/US2016/054788, dated Jun. 7, 2017, 17 pages.
(Continued)

*Primary Examiner* — Kevin T Truong
*Assistant Examiner* — Tracy L Kamikawa
(74) *Attorney, Agent, or Firm* — Duane Morris LLP (57) ABSTRACT

A system comprises a first implant including first and second screw receiving holes having respective first and second longitudinal axes. A second implant includes third and fourth screw receiving holes having respective third and fourth longitudinal axes. First and second drill guides have respective fifth and sixth longitudinal axes. A targeting guide is provided for aligning the first and second drill guides with each of the first and second implants simultaneously, so that the first, third and fifth longitudinal axes lie along a same line as each other, and the second, fourth and sixth longitudinal axes lie along a same line as each other.

13 Claims, 10 Drawing Sheets

(56) References Cited

U.S. PATENT DOCUMENTS

| | | | |
|---|---|---|---|
| 5,281,224 A | 1/1994 | Faccioli et al. | |
| 7,311,710 B2 | 12/2007 | Zander | |
| 8,679,130 B2 * | 3/2014 | Smith | A61B 17/00 606/96 |
| 8,709,092 B2 * | 4/2014 | Segina | A61B 17/1728 623/22.12 |
| 8,734,448 B2 * | 5/2014 | Thakkar | A61B 17/1721 606/64 |
| 9,089,375 B2 * | 7/2015 | Smith | A61B 17/808 |
| 9,138,245 B2 * | 9/2015 | Mebarak | A61B 17/17 |
| 2003/0097131 A1 | 5/2003 | Schon et al. | |
| 2006/0206044 A1 | 9/2006 | Simon | |
| 2007/0219636 A1 | 9/2007 | Thakkar | |
| 2009/0054992 A1 | 2/2009 | Landes et al. | |
| 2009/0157077 A1 | 6/2009 | Larsen et al. | |
| 2011/0251614 A1 | 10/2011 | Piraino | |
| 2011/0270328 A1 | 11/2011 | Overes | |
| 2014/0243837 A1 | 8/2014 | Mebarak | |
| 2015/0032168 A1 | 1/2015 | Orsak et al. | |
| 2015/0150568 A1 | 6/2015 | Powell | |
| 2016/0157900 A1 | 6/2016 | Simon | |

OTHER PUBLICATIONS

Wright Medical Technology,Inc., "VALOR, Hindfoot Fusion System", Surgical Technique Guide, Jun. 13, 2015, 37 pages.

* cited by examiner

TARGETING GUIDE AND METHOD FOR AN IMPLANT

CROSS-REFERENCE TO RELATED APPLICATION

This application is a U.S. national stage application under 35 U.S.C. § 371 of International Application No. PCT/US2016/054788, filed Sep. 30, 2016, the entirety of which is incorporated herein by reference.

FIELD

This disclosure relates to medical devices generally, and more specifically to devices used during surgical procedures.

BACKGROUND

An intramedullary (IM) nail is a metal rod inserted into the medullary cavity of a bone. IM nails are used to treat bone fractures of the body. IM nails advantageously promote healing while sharing the load with the bone into which it is implanted. IM nails have been used for treatment of relatively long bones, such as the talus, tibia and in some cases, the calcaneus.

SUMMARY

In some embodiments, a system comprises a first implant including first and second screw receiving holes. The first and second screw receiving holes have respective first and second longitudinal axes aligned with a transverse axis of the first implant. A second implant includes third and fourth screw receiving holes. The third and fourth screw receiving holes have respective third and fourth longitudinal axes aligned with a transverse axis of the second implant. First and second drill guides have respective fifth and sixth longitudinal axes. A targeting guide is provided for alignment of or positioning the first and second drill guides with each of the first and second implants, so that the first, third and fifth longitudinal axes are collinear with each other, and the second, fourth and sixth longitudinal axes are collinear with each other.

In some embodiments, a system comprises an intramedullary nail including first and second screw receiving holes. A bone plate includes third and fourth screw receiving holes. First and second drill guides are provided. A targeting guide is provided for aligning the first drill guide with the first and third screw receiving holes and for aligning the second drill guide with the second and fourth screw receiving holes simultaneously. The targeting guide holds the intramedullary nail, and the first and second drill guides are configured to engage and hold the bone plate.

In some embodiments, a method comprises: (a) attaching an end of a first implant to a targeting guide, the first implant having a first longitudinal axis; (b) inserting first and second drill guides in the targeting guide; and (c) attaching a second implant to the first and second drill guides, the second implant having a second longitudinal axis, so the first and second drill guides hold the second implant in a position with the second longitudinal axis parallel to the first longitudinal axis.

DETAILED DESCRIPTION

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

This disclosure provides a targeting guide that can be used for implanting a first implant, such as an IM nail, in a bone of a patient. In some embodiments, the targeting guide can be used to align drill guides for drilling pilot holes through bone to the side of the IM nail. In some embodiments, the drill guides hold and align a second implant, such as a bone plate, with the IM nail, so that bone screws inserted in the screw holes of the bone plate are coaxial with and engage screw holes in the side wall of the IM nail. This allows the surgeon to implant a frame structure including an IM nail, a parallel bone plate, and at least two bone screws connecting the IM nail and bone plate to each other, and to the bone, forming a strong structure.

Figure 1:
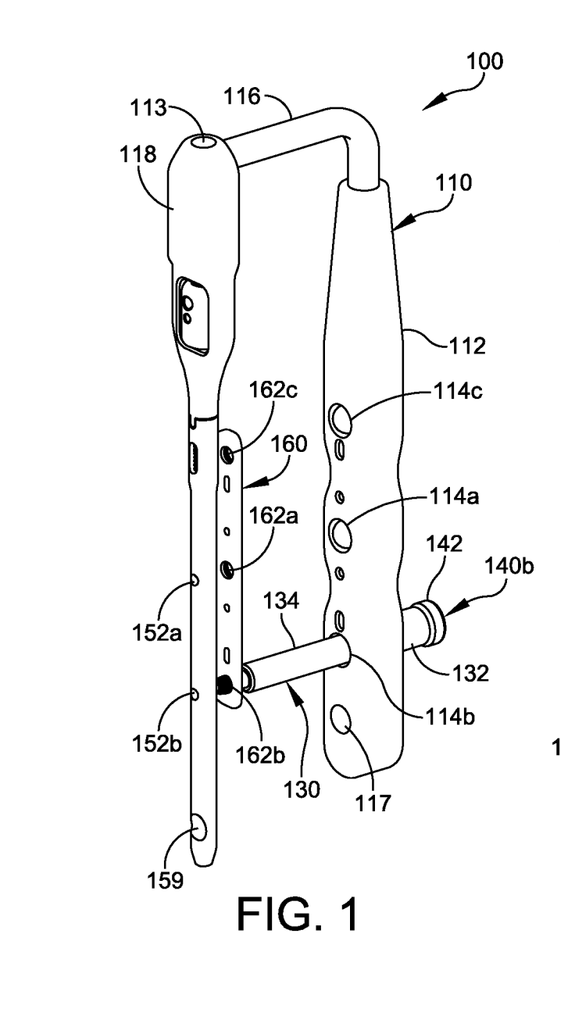
FIG. 1 is an isometric view of a system according to some embodiments.
Figure 2:
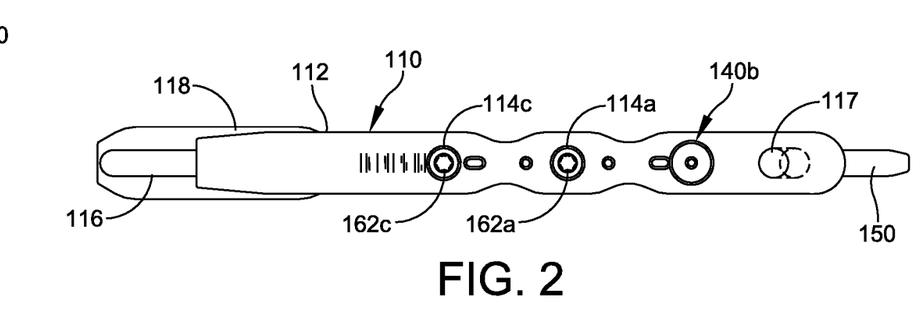
FIG. 2 is a top plan view of the system of FIG. 1.
Figure 3:
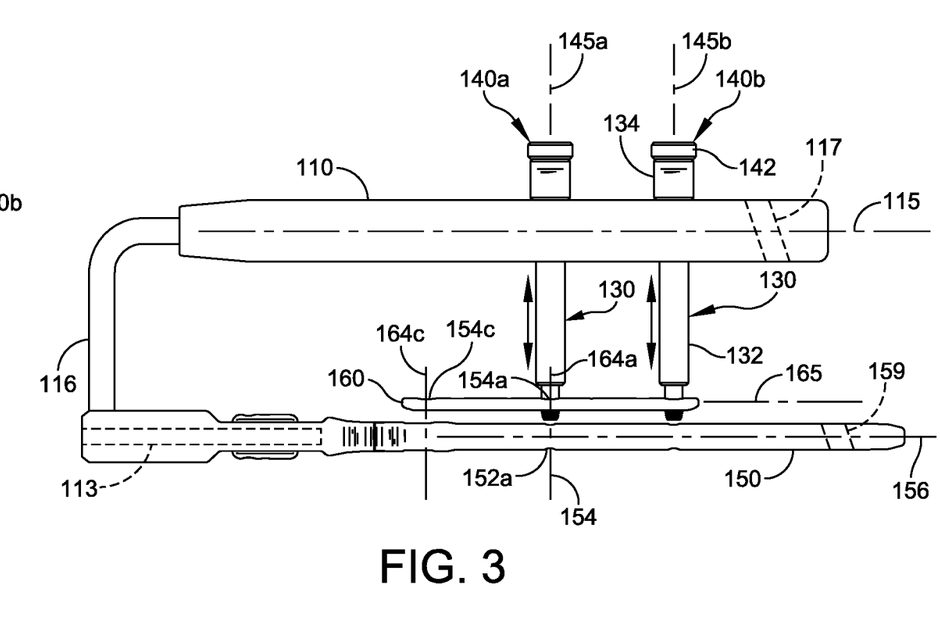
FIG. 3 is a front elevation view of the system of FIG. 1.

For example, in some embodiments, as shown in FIGS. 1-3, an intramedullary nail 150 (first implant) includes first and second screw receiving holes 152a, 152b. A bone plate 160 (second implant) includes third and fourth screw receiving holes 162a, 162b. The system has first and second drill guides 140a, 140b. A targeting guide 110 aligns the first drill guide 140a with the first 152a and third 162a screw receiving holes and for aligning the second drill guide 140b with the second 152b and fourth 162b screw receiving holes simultaneously. The targeting guide 110 supports the intramedullary nail 150, and the first and second drill guides 140a, 140b, respectively, are configured to engage and support the bone plate 160. In some embodiments, the first and second drill guides 140a, 140b, by themselves hold (support) the bone plate 160.

Figure 4:
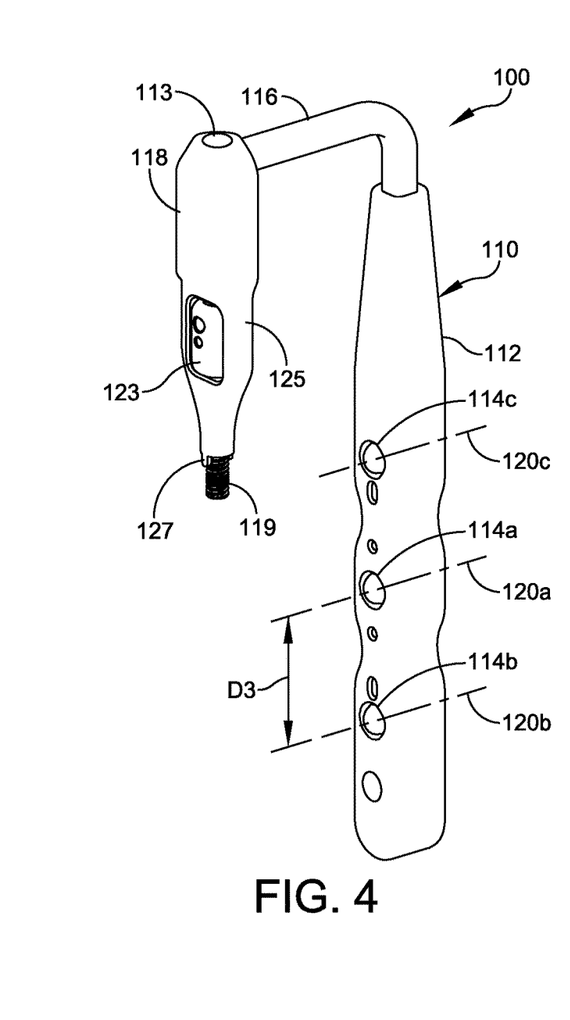
FIG. 4 is an isometric view of the targeting guide shown in FIG. 1.
Figure 5:
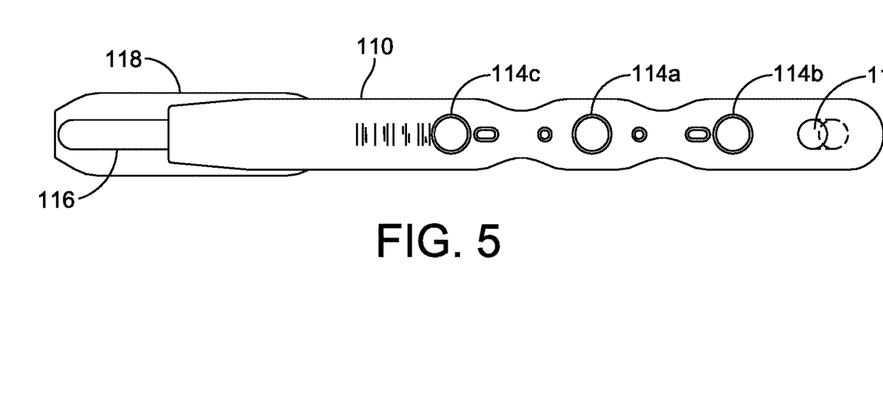
FIG. 5 is a top plan view of the system of the targeting guide of FIG. 4.
Figures 6, 6A:
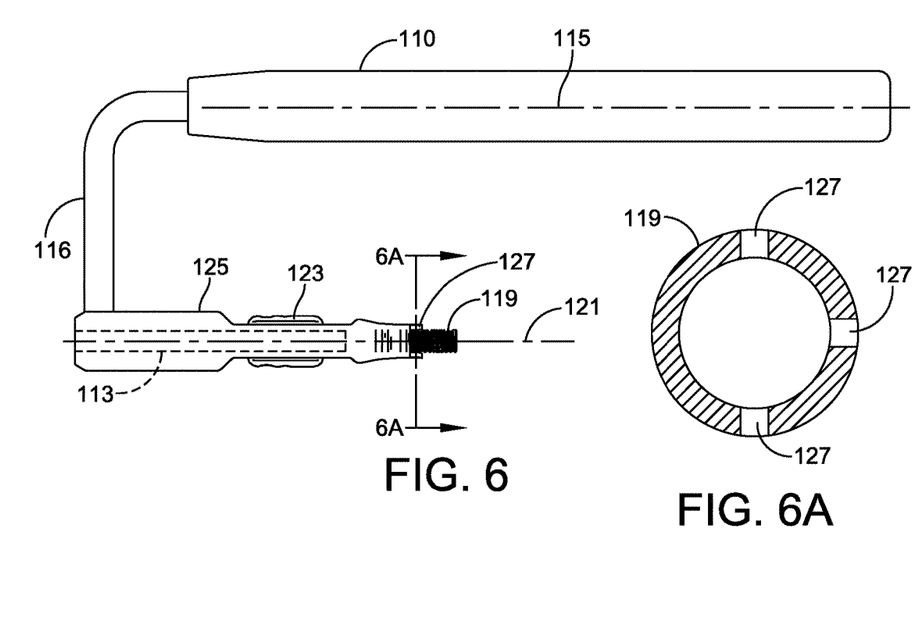
FIG. 6 is a cross-sectional view of the targeting guide of FIG. 4.
FIG. 6A is a cross sectional view taken across section line 6A-6A of FIG. 6.

FIGS. 4-6 show the targeting guide 110 of FIG. 1, according to some embodiments. The targeting guide 110 has a handle 112. The handle 112 has a longitudinal axis 115, illustrated in FIG. 6. In various embodiments, the handle 112 can have a cross section that is substantially square, rectangular, round, hexagonal, or the like. The handle 112 has two or more holes 114a, 114b. In some embodiments, the handle 112 has three holes 114a-114c. Other embodiments include additional holes for compatibility with a variety of implants. The holes 114a-114c have respective longitudinal axes 120a-120c. In some embodiments, the longitudinal axes 120a-120c are all parallel to each other and perpendicular to the longitudinal axis 115 of the handle 112. In other embodiments, the holes can be at an oblique angle with respect to the radial direction of the handle 112. For example, the handle 112 can have a hole 117 oriented at an oblique angle with respect to the axis 115 of the handle 112. The targeting guide 110 also has a threaded member 119 with a longitudinal axis 121 parallel to the longitudinal axis 115 of the handle 112. The threaded member 119 is fixedly attached to a thumb screw 123. The thumb screw 123 is contained within a housing 125 with openings to provide access to the thumb screw 123. The thumb screw 123 is rotatable about the axis 121. An offset member 116 fixes the offset distance of the thumbscrew 123, housing 125, and threaded member 119 relative to the handle 112. The offset member is sized larger than a maximum expected radial distance between an IM nail and a bone plate to be implanted using the targeting guide. The housing 125 is fixedly attached to the offset member 116, and neither translates nor rotates. The housing 125 has at least one tab 127 configured to engage a corresponding slot 157 (FIG. 7) of the IM nail 150. In some embodiments, the housing 125 has three tabs 127 arranged in a "T" configuration. In some embodiments, the housing 125 is cannulated, and has a central cannula 113 through which the surgeon can insert a set screw for engaging the inner threads 158 of the IM nail, to compress the IM nail radially outward adjacent the set screw.

Figure 7:
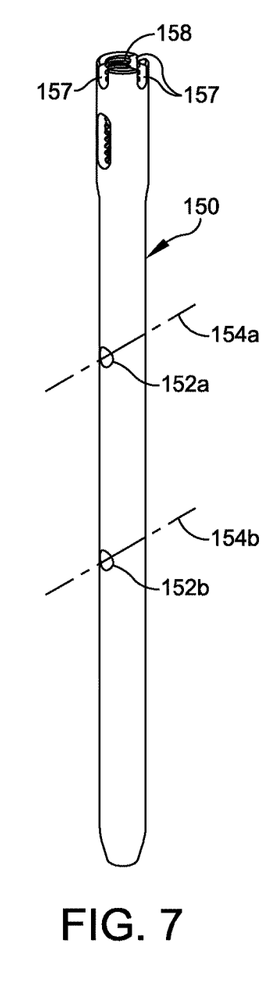
FIG. 7 is an isometric view of the intramedullary (IM) nail shown in FIG. 1.
Figure 8:
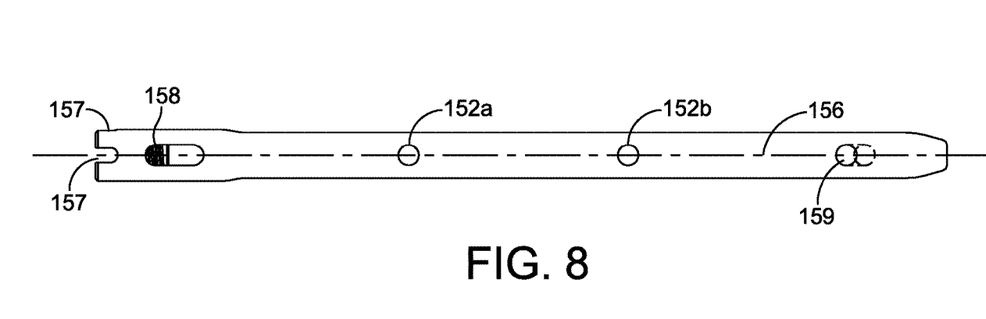
FIG. 8 is a top plan view of the IM nail of FIG. 7.
Figure 9:
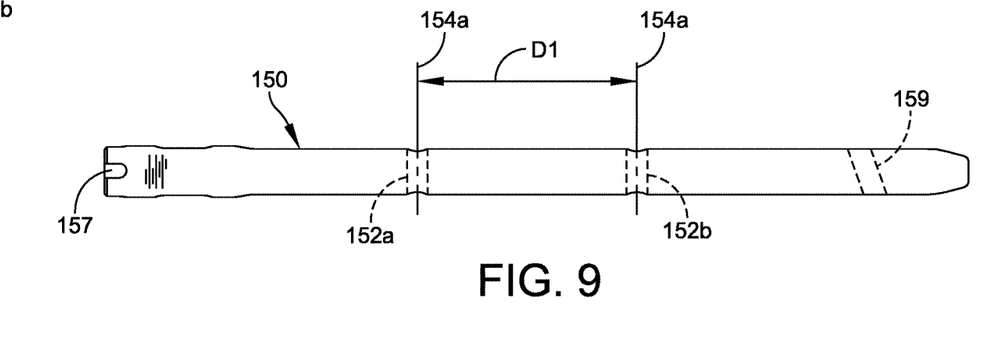
FIG. 9 is a front elevation view of the IM nail of FIG. 7.

FIGS. 7-9 show an example of the first implant 150. The first implant 150 includes first 152a and second 152b screw receiving holes having respective first 154a and second 154b longitudinal axes. In some embodiments, the axes 154a, 154b of the screw receiving holes 152a, 152b are perpendicular to the longitudinal axis 156 of the first implant. The holes 152a, 152b are separated by a center-to-center distance D1. In some embodiments, the first implant 150 has a hole 159 oriented at an oblique angle relative to the longitudinal axis 156. In FIGS. 7-9, the first implant 150 is an IM nail. The IM nail 150 has a corresponding (or first or second) thread 158 at one end for receiving the threaded member 119 of the targeting guide 110. The IM nail 150 has at least one slot 157 at the same end as the female thread 158 (or male thread, in an embodiment where the targeting guide 100 has a female thread (not shown) instead of the threaded member 119). The tabs 127 of the targeting guide 110 ensure rotational alignment of the IM nail 150 with respect to the handle. When the tabs 127 engage the slot 157, the axes 154a, 154b of the holes 152a, 152b coaxial with the axes 120a, 120b of the handle 112. In some embodiments, the first implant 150 has an additional hole with an axis (not shown) that aligns with the axis 120a of the handle 112. In some embodiments, as shown in FIGS. 6A and 7, the targeting guide 110 has three tabs 127 arranged in a "T" configuration, and the IM nail 150 has three corresponding slots. The "T" configuration ensures that the IM nail is rotated to the correct angle about longitudinal axis 156 (and about the longitudinal axis 121 of the targeting guide while the IM nail 150 is attached to the targeting guide.

Figure 10:
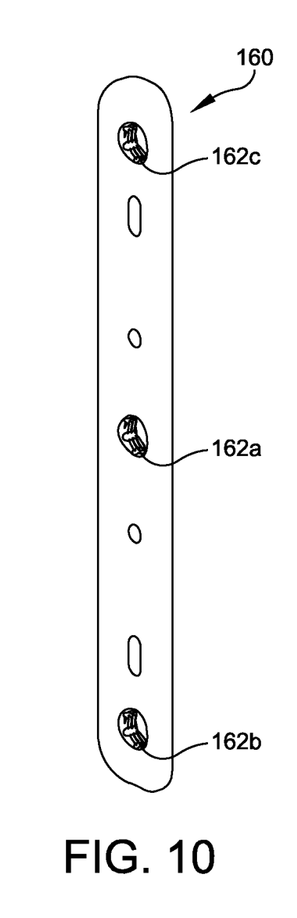
FIG. 10 is an isometric view of the bone plate shown in FIG. 1.
Figure 11:
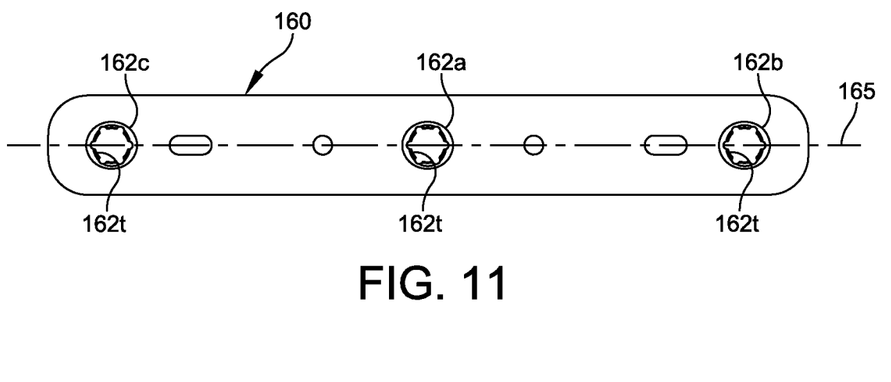
FIG. 11 is a top plan view of the bone plate of FIG. 10.
Figure 12:
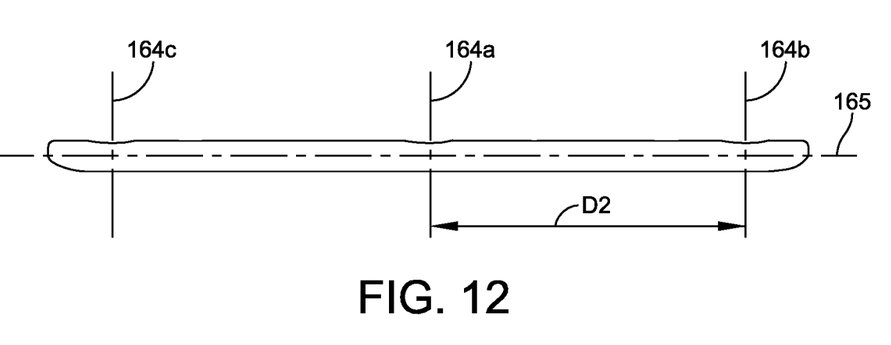
FIG. 12 is a front elevation view of the bone plate of FIG. 10.

A second implant 160 (FIGS. 10-12) includes third 162a and fourth 162b screw receiving holes having respective third 164a and fourth 164b longitudinal axes. The axes 164a, 164b of the screw receiving holes 162a, 162b are perpendicular to the longitudinal axis 165 of the second implant 160. The second implant can include any number of additional screw receiving holes. Although the exemplary second implant 160 has two axes of symmetry, the second implant can have zero, one or two axes of symmetry. The second implant 160 can have any shape. For some embodiments, at least two screw receiving holes 162a-162c of the second implant are separated by a center-to-center distance D2 (FIG. 12), where the distance D2 is the distance between the center of hole 162a and the center of hole 162b. In some embodiments, the distance D2 matches the center-to-center distance D1 (FIG. 9) between the holes 152a, 152b of the first implant (i.e., D2=D1). That is, the axes 164a and 164b are separated by the distance D2, and the axes 154a and 154b are separated by the distance D1. In some embodiments, the distance D2 is constant between each pair of adjacent holes 162a-162c, and the corresponding distance D1 is the same constant value. In other embodiments, the distance D2 varies among different pairs of holes 162a-162c, and the corresponding distances D1 also vary so the holes 152a-152c line up with the holes 162a-162c.

In some embodiments, the first 150 and second 160 implants have the same number of holes 152, 162 as each other. In other embodiments, either or both implants can have extra holes, so long as both implants have at least two holes, and the holes 152 of the first implant 150 are separated by the same center-to-center distance as the holes of the second implant (i.e., D2=D1) and the holes of the first and second implants can be simultaneously aligned.

Figure 13:
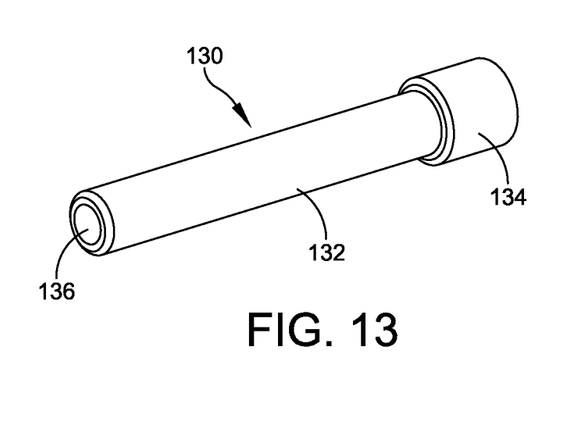
FIG. 13 is an isometric view of the sleeve shown in FIG. 1.
Figure 14:
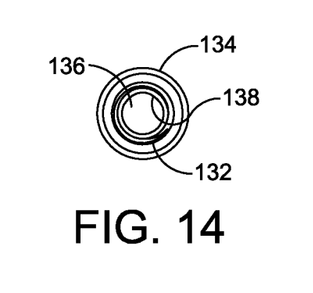
FIG. 14 is a top plan view of the sleeve of FIG. 13.
Figure 15:
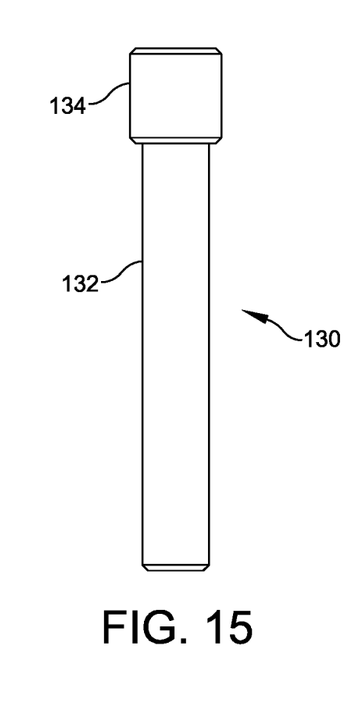
FIG. 15 is a front elevation view of the sleeve of FIG. 13.
Figure 16:
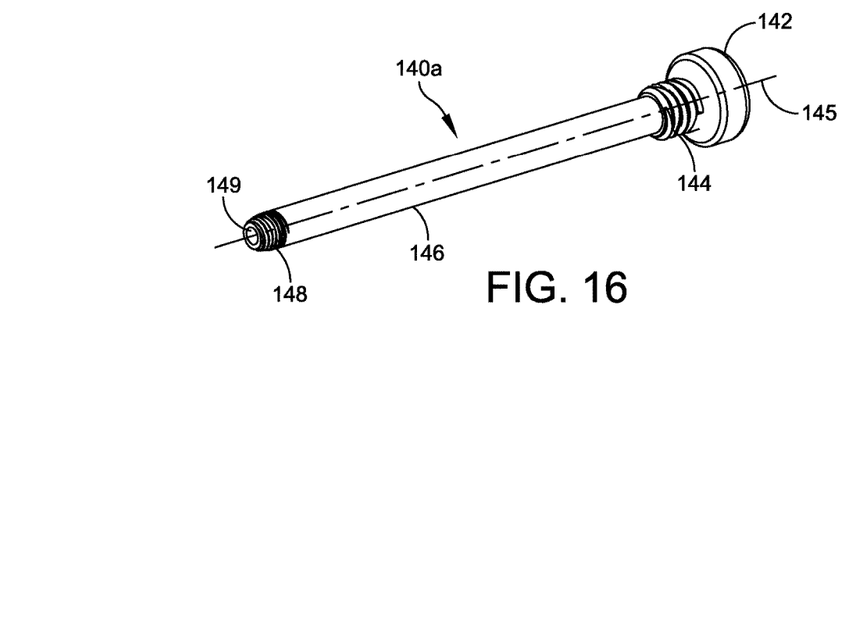
FIG. 16 is an isometric view of the drill guide shown in FIG. 1.
Figure 17:
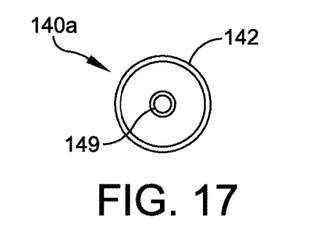
FIG. 17 is an end view of the drill guide of FIG. 16.
Figure 18:
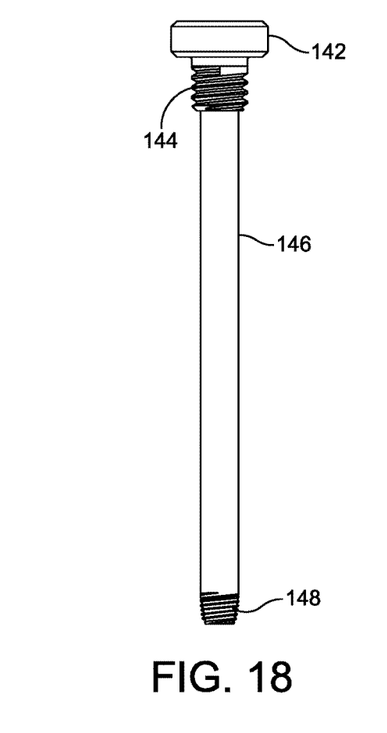
FIG. 18 is a front elevation view of the drill guide of FIG. 16.
Figure 19:
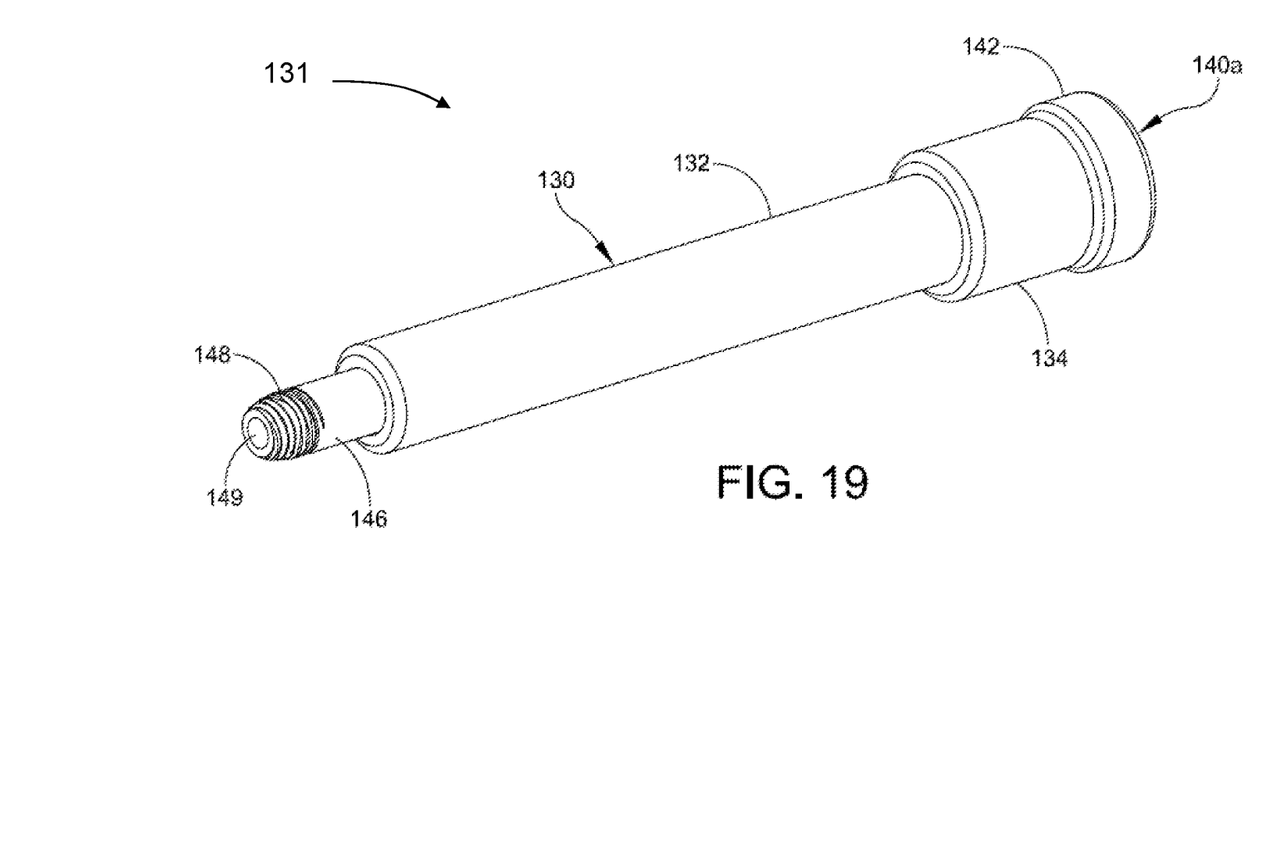
FIG. 19 is an isometric view of a drill guide and sleeve assembly as shown in FIG. 1.

FIG. 19 shows a drill guide device 140a, which can be a unitary device or a multi-component drill guide assembly 131. The second drill guide 140b can be identical to drill guide 140a, and can include identical components to drill guide 140a. For brevity, only the first drill guide 140a is described in detail. The drill guide assembly 131 includes a sleeve 130 and a drill guide 140a. FIGS. 13-15 show a sleeve 130. FIGS. 16-18 show a drill guide 140a. Each drill guide 140a is concentrically received in a respective sleeve 130.

As illustrated in FIGS. 16-18, the system includes at least first and second drill guides 140a, 140b having respective fifth and sixth longitudinal axes 145a, 145b, respectively. Each drill guide 140a, 140b has an elongated cylindrical tube 146 with an elongated cylindrical passage 149 extending along the entire length of the drill guide 140a, for guiding a drill bit (not shown). In some embodiments, the drill bit is marked with calibration markings, allowing the surgeon to determine the depth of the hole drilled into bone, and to determine when a predetermined hole depth is reached. FIG. 3 shows at least one drill guide 140b inside sleeve 130, which is slidably mounted in the holes 114b of the targeting guide 110. Second drill guide 140b is positioned as part of the system in a similar manner to the first drill guide 140a. The drill guides 140a, 140b engage the locking screw receiving hole 162a, 162b (FIGS. 10-12) of the second implant 160. In some embodiments, an additional drill guide (not shown) in a sleeve 130 can be slidably mounted in the remaining hole 114c, and engage a corresponding locking screw receiving hole 162c in the second implant 160. Alternatively, the drill guides 140a-140b in respective sleeves 130 can be slidably mounted in holes 114a, 114b and engage the locking screw receiving hole 162a, 162b of the second implant 160. In other embodiments, the drill guides 140 in sleeves 130 can be slidably mounted in holes 114a, 114b and engage the locking screw receiving hole 162a, 162b of the second implant 160. The drill guide device 140a or 140b has a cylindrical passage extending throughout an entire length of the drill guide, from the threaded end 148 of the first tubular section 146 to an end of the drill guide device 140a opposite the threaded end. The cylindrical passage 149 has an inner diameter smaller than the first outer diameter. The cylindrical passage 149 is adapted to receive and align a drill (not shown) for drilling bone 170.

In some embodiments, the first and second drill guides 140a, 140b have threaded portions 148 at respective ends thereof opposite the head 142 of each drill guide 140a, 140b, and the third 162a, and fourth 162b screw receiving holes of the second implant 160 each have mating threads 162t for engaging the threaded portions 148. Further, the drill guide 140a, 140b may be tubular, and forms a first tubular section of the drill guide assembly 131.

The sleeves 130 have smooth cylindrical outer surfaces configured to be slidably mounted in the holes 114a-114c in the handle 112 of targeting guide 110. Each sleeve 130 can hold a drill guide 140a, 140b, and is also capable of inserting a screw with a self-retaining driver through the sleeve 130 after the drill guide 140a, 140b is removed from the sleeve. Each of the first and second drill guides 140a, 140b is configured to be concentrically held inside a respective one of the first and second sleeves 130. In some embodiments, each drill guide 140a, 140b has a thread 144 (second thread) adjacent the head 142 of the drill guide 140a, 140b, and each sleeve 130 has a respective inner thread 138 for threadably receiving the thread 144 of its respective drill guide 140a, 140b. The threads 138 and 144 maintain the drill guide 140a, 140b inside the sleeve regardless of the orientation of the targeting guide 110. In other embodiments (not shown), the thread 144 is omitted from the drill guides 140a, 140b, and the inner thread 138 is omitted from the sleeve 130; the drill guide 140a, 140b is slidably received in the sleeve 130.

In some embodiments, each sleeve 130 has a second tubular section 132 and a respective shoulder (third tubular section) 134 for retaining the sleeve 130 within a respective opening 114a-114c of the targeting guide 110. The second tubular section 132 has a second outer diameter greater than the first outer diameter of the drill guide. The second tubular section 132 is configured to be slidably received within a respective opening 114a-114c of the targeting guide 110. The opening 114a-114c of the targeting guide 110 is adapted to be aligned with the threaded opening 162a, 162b in the bone implant 160. With the shoulder 134 of each sleeve 130 abutting the handle 112 of the targeting guide 110, and the head of each drill guide 140a, 140b abutting its respective shoulder 134, the drill guides 140a, 140b and second implant 160 are fully supported for hanging from the handle 112.

In other embodiments (not shown) the drill guide 140a, 140b and sleeve 130 are unitary devices, each formed from a single piece of material.

The first and second drill guides 140a, 140b have threaded portions 148 at respective ends thereof. Each of the screw receiving holes 162a-c can have mating threads 162t for engaging the threaded portions 148 of the drill guides 140a, 140b.

The targeting guide 110 is configured for aligning the drill guides 140a, 140b with each of the first 150 and second 160 implants simultaneously, so that the first axis 152a (of the first implant 150), third axis 162a (of the second implant 160) and fifth longitudinal axes 145a (of the drill guide 140a, 140b) lie along a same line as each other, and the second 152b, fourth 162b and sixth longitudinal axes 145b lie along a same line as each other. Thus, the center-to-center distance D3 between the axes 120a, 120b of holes 114a, 114b of the handle 112 matches the distance D1 of the first implant 150 and the distance D2 of the second implant 160.

The targeting guide 110 supports the first implant 150, and the first and second drill guides 140a, 140b are configured to engage and support the second implant 160, without direct contact between the second implant 160 and any other object except the first and second drill guides 140a, 140b. This arrangement allows the second implant 160 to slide freely in one direction (vertical direction in FIG. 3), parallel to the longitudinal axes 145a, 145b of the drill guides 140a, 140b. This direction of sliding movement is perpendicular to the longitudinal axis 156 of the first implant 150 and the longitudinal axis 165 of the second implant 160. For example, as shown in FIG. 3, the drill guides 140a, 140b hold a second implant (bone plate) 160 parallel to the first implant (IM nail) 150, and the second implant 160 can move up and down relative to the first implant 150 for positioning the second implant.

In some embodiments, the first implant is an IM nail 150, the second implant is a bone plate 160, and the IM nail 150 and the bone plate 160 have respective longitudinal axes 156, 165, and the targeting guide 110 is configured to support the bone plate 160 with the longitudinal axis 165 of the bone plate 160 parallel to the longitudinal axis 156 of the IM nail 110.

In some embodiments, the targeting guide 110 has a threaded member 119, to detachably attach a distal end of the intramedullary nail 150 having a female thread 158 to the targeting guide, so the first axis 154a of the screw receiving hole 152a of the IM nail 150 is aligned with the fifth axis 145a of the first drill guide 140a, 140b, and the second axis 154b of the IM nail is aligned with the sixth axis 145b of the second drill guide. In some embodiments, the threaded member 119 is cannulated for screw driver access. This allows the surgeon to drive a set screw (not shown) into the female thread 158 of the IM nail 150, to compress the IM nail.

In some embodiments, the drill guides 140a, 140b in their sleeves 130 are slidably mounted in the targeting guide 110, for moving the bone plate 160 relative to the intramedullary nail 150.

The targeting guide can be made from a variety of materials. In some embodiments, the targeting guide comprises plastic, so the targeting guide does not show up in a fluoroscopic image during surgery. The implants and drill guides can be made of metal (e.g., titanium, stainless steel), so as to appear in a fluoroscopic image during surgery.

Although an example is described as having two drill guides, in some embodiments, only one drill guide may be used, while in other embodiments, three drill guides may be used. The targeting guide 100 can have additional holes 114, in which case more than three drill guides can be used simultaneously.

Operation

In some embodiments, a method of using the targeting guide comprises attaching an end of a first implant 150 to a targeting guide 110. The first implant 150 has a first longitudinal axis 156. For example, the threaded member 119 of the targeting guide can be inserted in the distal end of the IM nail 150 with the tabs 127 of the targeting guide aligned with the slot 157 of the IM nail 150. The thumb screw 123 is rotated to secure the threaded member 119 inside the inner thread 158. Once tabs 127 engage the slot 157, and the thumb screw 123 is tightened, the IM nail 150 cannot translate or rotate relative to the targeting guide 110, and the holes 152a, 152b of the first implant are coaxial with the holes 114a, 114b of the targeting guide 110.

The drill guide assemblies are assembled by screwing each drill guide 140a, 140b into its respective sleeve 130, so the thread 144 of the drill guide engages the inner thread 138 of the sleeve 130. If a unitary drill guide/sleeve structure is used, this assembly step is omitted. Each of the first and second drill guide assemblies are inserted in the targeting guide 110. In some embodiments, the drill guide assemblies are assembled and inserted into the targeting guide 110 before the first implant 150 is attached to the targeting guide.

The second implant 160 is attached to the first and second drill guides 140a, 140b. For example, the threaded member 148 of each drill guide engages the respective screw receiving hole 162a, 162b of the second implant. The third screw receiving hole 162a receives the threaded portion 148 of the first drill guide 140a, and the forth screw receiving hole 162b receives a threaded portion 148 of the second drill guide 140b. The first and second drill guides 140a, 140b hold the second implant 160 in a position with the second longitudinal axis 165 (of the second implant 160) parallel to the first longitudinal axis 156 of the first implant 150. The axes 156 and 165 are in the same plane as axes 145a-145b, 154a-154c and 164a-164c. Within that plane, axes 156 and 165 are perpendicular to axes 145a-145b, 154a-154c and 164a-164c. In some embodiments attachment of the first implant 150 to the threaded member 119, insertion of the drill guide assemblies into the holes 114a-114c of the handle 112 and attaching the second implant 160 to the drill guides 140a, 140b aligns the first drill guide 140a with a first screw receiving hole 152a in the first implant 150 and a third screw receiving hole 162b in the second implant 160, and aligns the second drill guide 140b with a second receiving hole 152b in the first implant 150 and a fourth screw receiving hole 162b in the second implant 160. In some embodiments, the drill guide assemblies are assembled and inserted into the targeting guide 110, and the second implant 160 is attached to the drill guides 140a, 140b, before the first implant 150 is attached to the targeting guide.

The surgeon makes an incision on a dorsal or plantar side of the foot to get access to the bones. The surgeon drills a longitudinal hole into the bone to be repaired, using a k-wire, for example. The bone 170 can be a metatarsal, a hind foot bone, a femur or other bone. In some embodiments, the IM nail 150 is inserted into the medial column of a Charcot foot.

Figure 20:
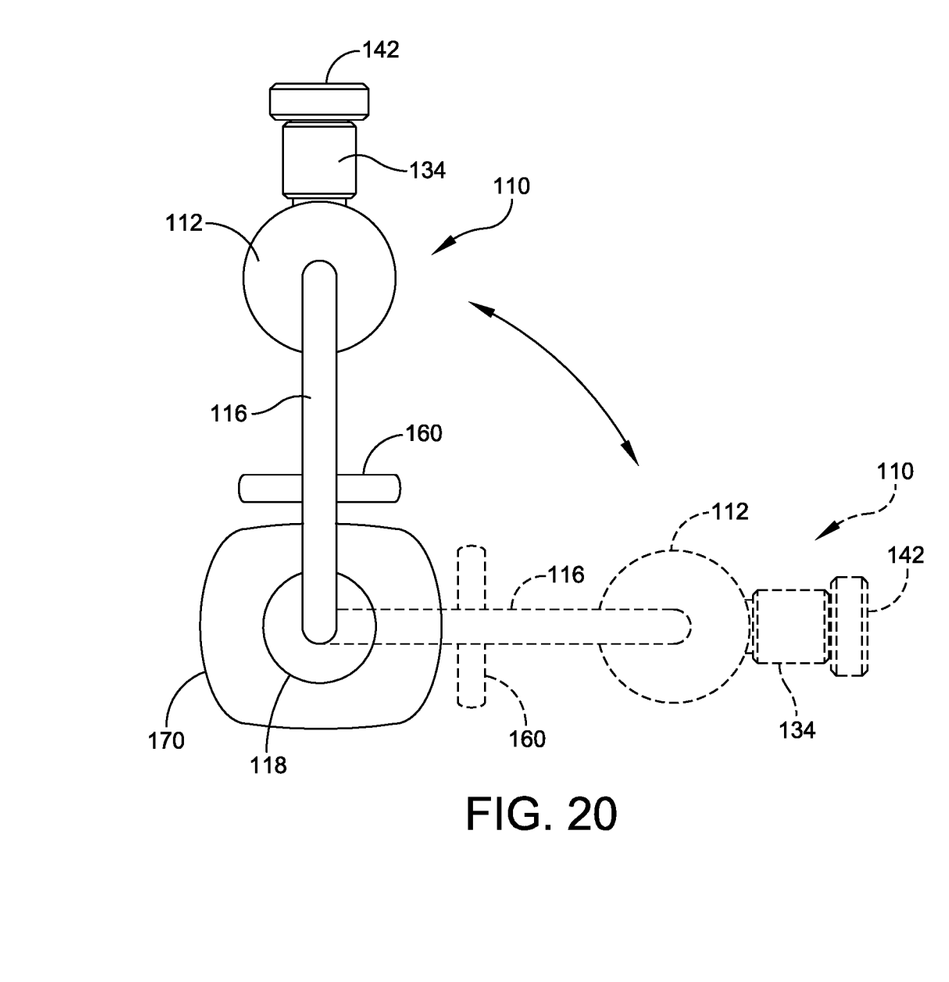
FIG. 20 is an anterior end view of the system of FIG. 1, showing rotation to position the bone plate.

The targeting guide 110 can be rotated around the first longitudinal axis 156 of the intramedullary nail 150 after inserting the IM nail 150 into the bone 170. FIG. 20 shows rotation of the targeting guide 110 around the IM nail (hidden behind the housing 118 in the anterior view of FIG. 20). The bone plate 160 can be located on the dorsal, medial, or plantar side of the foot, or in between, depending on the structure and quality of the bones. The surgeon makes a dorsal, medial or plantar incision (depending on where the plate 10 will be located). Once the bone plate 160 is in the desired position, the surgeon slides the drill guides 140a, 140b towards the wound site, and the bone plate drops onto the bone 170. The surgeon inserts the drill bit (not shown) into the cylindrical passage 149 of each drill guide 140a, 140b and drills the holes along the longitudinal axis 145 of the drill guides, penetrating into bone 170 all the way to the screw receiving holes 152a, 152b of the IM nail. The size of the holes drilled corresponds to the inner diameter of the bone screws to be inserted into the plate 160.

In some embodiments, one drill guide 140a and sleeve 130 are removed from the targeting guide 110, while the bone plate 160 remains attached to the other drill guide 140b. A first bone screw 172 (FIG. 21) is inserted through the first screw receiving hole 162a of the bone plate 160, through the bone 170 and into the third screw receiving hole 152a of the IM nail 150. In some embodiments, the drill guide 140a is removed from one sleeve 130, and the first bone screw 172 (FIG. 21) is inserted through the sleeve 130. Once the first bone screw is securely tightened, the remaining drill guide 140b is removed from the plate 160, and the drill guide 140b is removed. The second bone screw is inserted through the second screw receiving hole 162b of the bone plate 160, through the bone 170 and into the fourth screw receiving hole 152b of the IM nail 150. In some embodiments, the second bone screw 172 is inserted through the second sleeve 130, and then the second sleeve is removed. After the second bone screw is inserted, the second sleeve 130 and the targeting guide 110 are removed.

Figure 21:
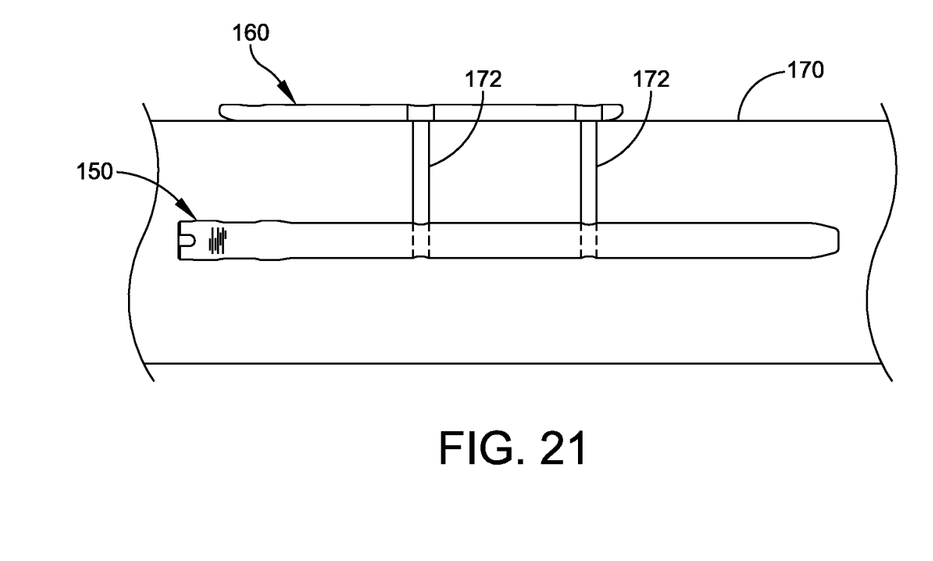
FIG. 21 is a cross-sectional view showing a bone with an IM nail and bone plate implanted.

FIG. 21 shows an example of a bone 170 having an IM nail 150 implanted therein, with an aligned bone plate 160 on the outer surface of the bone. Bone screws 172 penetrate the aligned screw receiving holes of the first 150 and second 160 implants providing improved support for the bone. Although FIG. 21 shows a single bone 170 for ease of explanation, the IM nail and bone plate construct can be implanted across two or more bones. For example, the IM nail can be implanted in the medial column, and pass from the first metatarsal to the talus.

An example is described above in which the first implant 150 is an IM nail and the second implant 160 is a bone plate. In other embodiments, different implants can be used. For example, in some embodiments, the first implant 150 and the second implant 160 are both bone plates. In other embodiments, the first implant 150 and the second implant 160 are both IM nails. In another embodiment (not shown), the targeting guide can have a second handle 112 opposite the first handle, with the threaded member 119 centrally located therebetween, for implanting two bone plates and an IM nail.

Figure 22:
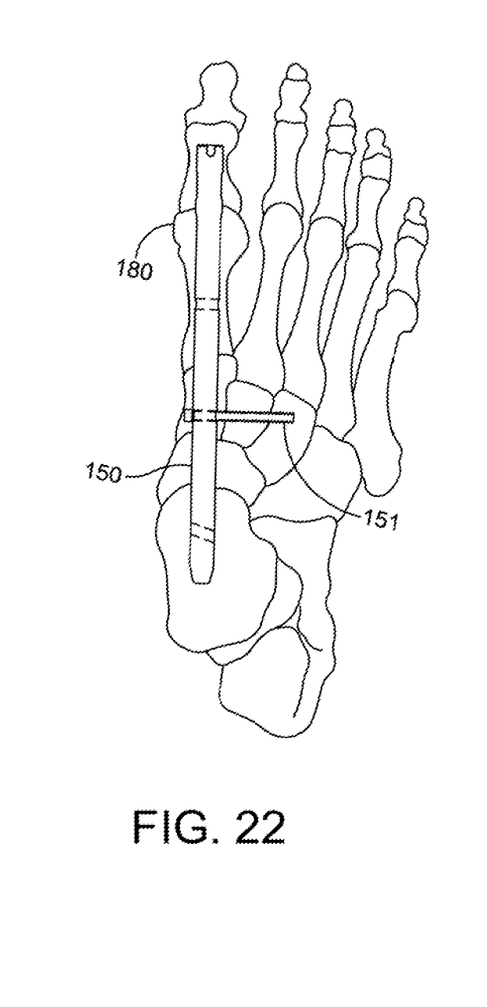
FIG. 22 is a schematic superior view of a foot having an IM nail and a screw implanted using the targeting guide.

For example, FIG. 22 is a schematic diagram showing a superior view of a foot 180. The first implant 150 is an implanted along the medial column, and can be an IM nail 150 as described above in the description of FIGS. 7-9. The second implant can be a screw 151, nail or the like. The screw 151 can be inserted perpendicular to the longitudinal axis of the IM nail 150 and extend through one of the holes 152a-152c, using a long drill bit to drill a pilot hole in the bone in the manner described above. The drill and drill guide 140a are removed from the sleeve 130. The screw 151 is then inserted through the sleeve 130 into bone. In the example of FIG. 22, the second implant 151 can be inserted across the mid-foot, and can be implanted in the cuneiform and/or navicular, for example.

Figure 23A:
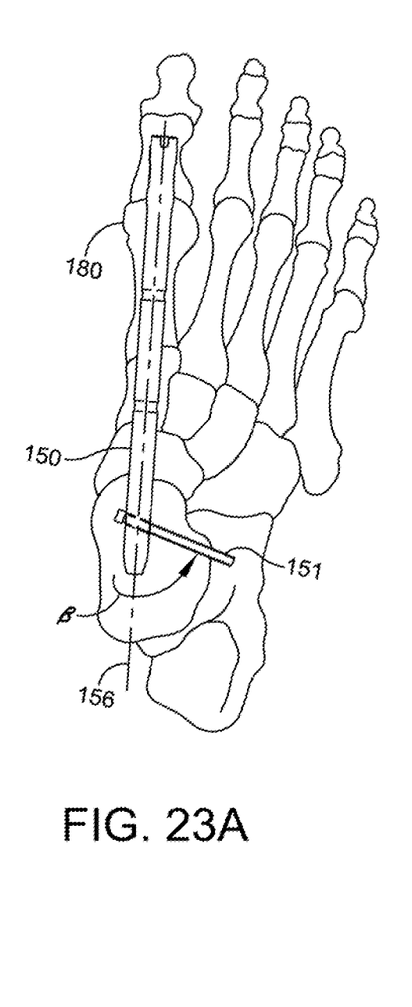
FIGS. 23A and 23B are schematic superior and medial views of a foot having an IM nail and obliquely oriented screw implanted using the targeting guide.
Figure 23B:
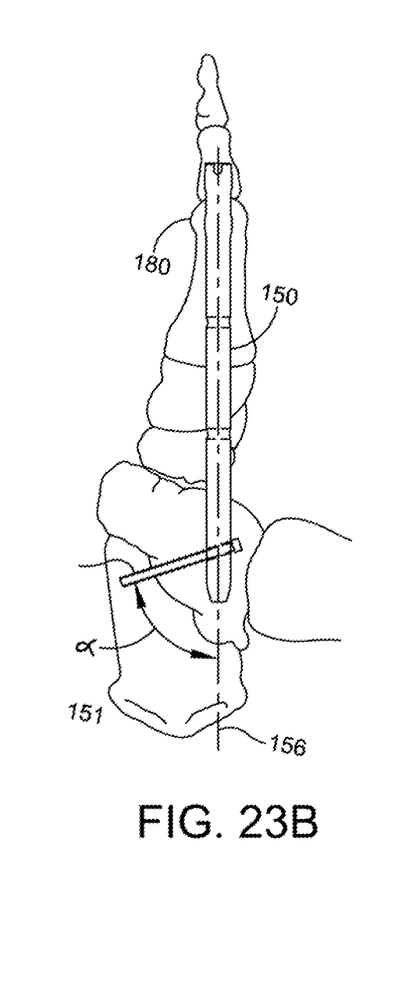

FIGS. 23A and 23B schematically show another example. FIG. 23A is a superior view, and FIG. 23B is a medial view. The first implant 150 can be an IM nail, inserted in the manner discussed above. The second implant 151 can be a screw, nail or the like. The second implant 151 can be inserted using the obliquely oriented hole 117 of the targeting guide 110 (FIG. 3), for a subtalar fusion, for example. The obliquely oriented hole 117 of the targeting guide 110 is arranged to orient the drill guide assembly 131 for drilling a pilot hole at an angle α (FIG. 23B) with respect to the longitudinal axis 156 of the IM nail 150. As shown in FIG. 23A, once the IM nail 150 is inserted into bone, the IM nail 150 and attached targeting guide 110 can be rotated by an angle β about the longitudinal axis 156 of the longitudinal nail. In this manner, the second implant 151 can be positioned in a non-sagittal, non-transverse plane. That is, a plane containing implants 150 and 151 is not oriented in a sagittal direction, and is not oriented in a transverse direction. A drill guide assembly 131 including a sleeve 130 and drill guide 140a is inserted into the hole 117. The hole 117 of the targeting guide and the hole 159 of the IM nail 150 are aligned. When the drill bit is inserted through this obliquely oriented drill guide 140a, the drill bit can penetrate bone till the hole 159 is reached. Once the pilot hole is drilled, the drill bit and drill guide 140a are removed, and the second implant (e.g., screw) 151 can be inserted through the sleeve 130, into the pilot hole. In this manner, the second implant 151 can be inserted into the talus and calcaneus, for example.

Although the subject matter has been described in terms of exemplary embodiments, it is not limited thereto. Rather, the appended claims should be construed broadly, to include other variants and embodiments, which may be made by those skilled in the art.

What is claimed is:

1. A system comprising:
    a first implant including first and second screw receiving holes, the first and second screw receiving holes having respective first and second longitudinal axes aligned with a respective transverse axis of the first implant;
    a second implant including third and fourth screw receiving holes, the third and fourth screw receiving holes having respective third and fourth longitudinal axes aligned with a respective transverse axis of the second implant;
    first and second drill guides having respective fifth and sixth longitudinal axes, wherein the first and second drill guides are configured to be coupled to the third and fourth screw receiving holes of the second implant so that the third and fifth longitudinal axes and the fourth and sixth longitudinal axes are collinear with each other; and
    a targeting guide configured to be directly coupled to the first implant, the first drill guide, and the second drill guide so that the first, third and fifth longitudinal axes are collinear with each other, and the second, fourth and sixth longitudinal axes are collinear with each other, wherein the targeting guide is not directly coupled to the second implant, and wherein the first and second drill guides are slideable in a direction parallel to the fifth and sixth longitudinal axes to adjust a distance between the first implant and the second implant.

2. The system of claim 1, wherein the first and second drill guides extend through each of the second implant and the targeting guide simultaneously.

3. The system of claim 1, wherein the targeting guide includes at least a first drill guide hole.

4. The system of claim 3, wherein the first drill guide hole is configured for receipt of the first drill guide.

5. The system of claim 1, wherein the targeting guide alone holds the first implant.

6. The system of claim 5, wherein at least one of the first and second drill guides has a distal threaded portion at a respective end thereof, and a respective one of the third and fourth screw receiving holes has mating threads for engaging the threaded portion.

7. The system of claim 5, wherein the first implant is an intramedullary nail, and the second implant is a bone plate.

8. The system of claim 7, wherein the intramedullary nail and the bone plate have respective longitudinal axes, the longitudinal axes of the intramedullary nail and the bone plate being perpendicular to the first, second, third, and fourth longitudinal axes.

9. The system of claim 8, wherein the system is configured to support the bone plate with the longitudinal axis of the bone plate parallel to the longitudinal axis of the intramedullary nail.

10. The system of claim 7, wherein the drill guides are slidably positioned in the targeting guide, for moving the bone plate relative to the intramedullary nail.

11. The system of claim 7, wherein the targeting guide with the intramedullary nail attached thereto can rotate around a longitudinal axis of the intramedullary nail.

12. The system of claim 7, wherein the first and second drill guides comprise first and second sleeves slidably mounted in the targeting guide and respective first and second drill guide inserts, each of the first and second drill guide inserts is concentrically held inside a respective one of the first and second sleeves.

13. The system of claim 12, wherein each sleeve of the first and second sleeves has a respective shoulder for retaining the sleeve within a respective opening of the targeting guide.

* * * * *